United States Patent [19]

Söderberg

[11] Patent Number: 4,995,810
[45] Date of Patent: Feb. 26, 1991

[54] TOOL FOR A PROSTHETIC PART

[75] Inventor: Per Olof Söderberg, Stockholm, Sweden

[73] Assignee: Astra Meditec Aktiebolag, Molndal, Sweden

[21] Appl. No.: 424,270

[22] PCT Filed: Apr. 22, 1988

[86] PCT No.: PCT/SE88/00206
§ 371 Date: Oct. 20, 1989
§ 102(e) Date: Oct. 20, 1989

[87] PCT Pub. No.: WO88/08283
PCT Pub. Date: Nov. 3, 1988

[30] Foreign Application Priority Data

Apr. 22, 1987 [SE] Sweden .................. 8701652

[51] Int. Cl.⁵ .................................. A61C 3/00
[52] U.S. Cl. ........................ 433/141; 433/174
[58] Field of Search ............. 433/174, 141, 225; 81/436, 447, 459

[56] References Cited

U.S. PATENT DOCUMENTS 4,234,309 11/1980 Sellers .................. 433/174
4,553,942 11/1985 Sutter .................... 433/225

FOREIGN PATENT DOCUMENTS 2133693 8/1984 United Kingdom ........ 433/225

Primary Examiner—Cary E. Stone
Attorney, Agent, or Firm—White & Case

[57] ABSTRACT

A tool is described, which is intended for screwing into place a threaded prosthetic part (6). The tool comprises a turning bolt (1) which has an elongated cylindrical core (2) having at one end thereof a head (3) for turning the tool, and having at its opposite end a portion (4) first threads (5) for fitting into threads in the prosthetic part, and is characterized in that the core has second threads (11), on a portion (10) thereof between the ends thereof, said second threads having a pitch direction opposite to the pitch direction fo the first threads, and a sleeve (13) arranged around the core, said sleeve having threads engaging said second threads, whereby the sleeve may be screwed into contact with the prosthetic part (6) locking the tool in the prosthetic part.

2 Claims, 2 Drawing Sheets

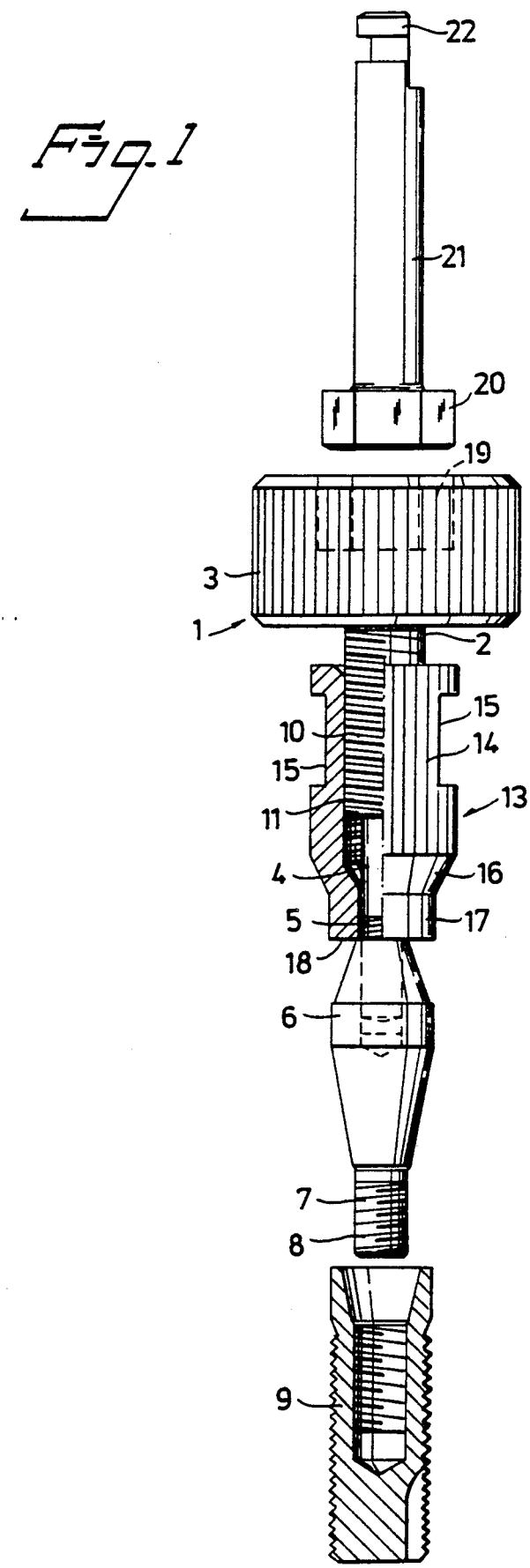

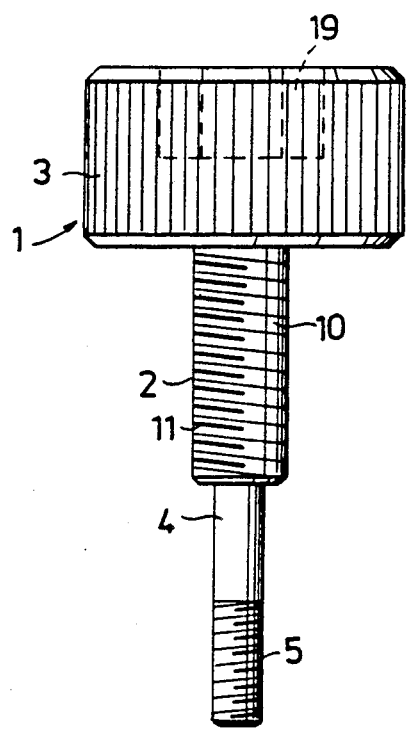
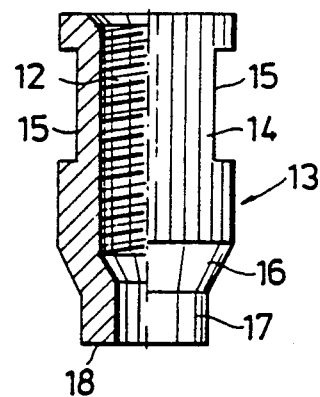
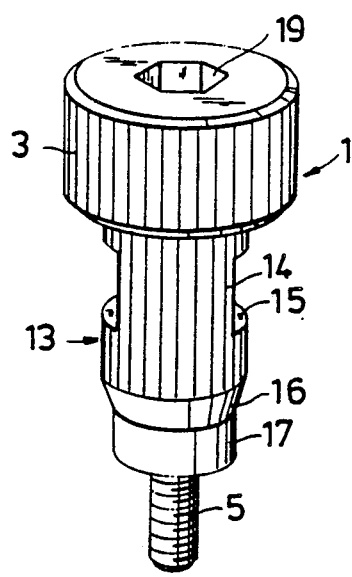

TOOL FOR A PROSTHETIC PART

TECHNICAL FIELD

The present invention is related to a tool for screwing into place a threaded prosthetic part (6), such as a part of a dental implant. The object of the invention is to provide a tool by which a prosthetic part having no grip means may be gripped, screwed into place and released from the tool in a simple manner.

STATE OF THE ART

From Adell et al., Int. J. Oral Surg. 10 (1981) page 388 a dental implant system is known comprising a root screw or fixture (a), a distance screw (d) and a gold cylinder (k). The root screw is intended to be screwed into a hole taken up in the jaw bone of a patient, and the distance screw is intended to be screwed into a hole in the root screw. For screwing into place, the root screw and the distance screw are both provided, at the upper ends thereof, with projecting hexagonal wrench abutments which may be gripped with a wrench having a corresponding recess. The making of such wrench abutments is a cost-raising fine-mechanical work operation in manufacture of said parts. The wrench abutments further have to be covered by the vaulted head of a screw or a plastic cap in order not to irritate the tissues of the oral cavity.

From WO No. 85/02337 an implant system is known comprising a root screw 1 and a pillar 6, neither of which having special grip means. For quick and easy attachment of said parts there is, however, a need for a tool.

DESCRIPTION OF THE INVENTION

According to the present invention there is provided a tool of the kind referred to initially above, which fulfils the object presented above. The tool comprises a turning bolt which has an elongated cylindrical core having at one end thereof a head for turning the tool, and having at its opposite end a portion with first threads for fitting into threads in the prosthetic part. The tool is characterized in that the core has second threads on a portion thereof between the ends thereof, said second threads having a pitch direction opposite to the pitch direction of the first threads, and a sleeve arranged around the core, said sleeve having threads engaging said second threads, whereby the sleeve may be screwed into contact with the prosthetic part and to lock the tool in the prosthetic part.

The tool is primarily intended for screwing into place a part of a dental implant, such as root screw which is screwed into a hole taken up in the jaw bone, or another part, which in turn is to be attached to the root screw, e.g. a distance element. The first threads should have the same pitch direction as the threads by which the prosthetic part is screwed into its place of attachment. For all practical purposes, all these threads are normal right-handed threads, which means that the second threads arranged on the tool are left handed threads.

According to a preferred embodiment of the invention, the tool is characterized in that the second threads are arranged on a portion of the core having a greater diameter than the threaded end, and that the sleeve arranged around the core has a main portion in which the threads are arranged, and an end portion having a reduced diameter adjacent to the threaded end portion of the core.

The end of the sleeve adjacent to the threaded end of the core has a contact surface shaped for fitting against the prosthetic part to be screwed into place. The contact surface of the socket may thus be e.g. planar, inwardly conical or outwardly conical.

The invention will be further described with reference to the appended drawings, wherein:

FIG. 1 is an exploded view showing a tool according to the invention together with prosthetic parts and a connector, FIG. 2 is a side view of a turning bolt for the tool in FIG. 1, FIG. 3 shows a sleeve, partly in section, for the tool in FIG. 1, and FIG. 4 shows a tool according to the invention at an oblique view from above.

In the drawings 1 denotes a turning bolt having an elongated cylindrical core 2 with a head 3 at one end thereof. The opposite end of the core has a cylindrical portion 4 having at the outer end thereof outward right-handed threads 5, which in FIG. 1 are in engagement with fitting inward threads in a pillar 6 serving as a distance element, which pillar is intended to carry a dental prosthesis. The pillar has, at the opposite end thereof, a cylindrical portion 7 provided with outward right-handed threads 8 by which it may be screwed into corresponding threads in a root screw 9. The root screw 9 in turn has outward right-handed threads by which it may be screwed into and osseo-integrated in a hole bored in the jaw-bone of a patient.

The core 2 of the turning bolt has a portion 10 adjacent to the head, which portion has a greater diameter than the end portion 4 and which is provided with outward left-handed threads fitting into corresponding inward threads 12 in a sleeve 13. The threads 12 are cut in the main portion 14 of the sleeve having on its outer surface two cut-recesses 15.

Via a conical portion 16 the main portion continues into an end portion 17 having reduced diameter, wherein the inner diameter is only slightly greater than the diameter of the threaded end portion 4 of the core. The sleeve has a planar end surface 18 by which it rests against the end of the pillar 6. In the upper end surface of the head of the turning bolt, there is a hexagonal recess 19, which may be put into engagement with the hexagonal head 20 of a connector 21 having at its opposite end attachment means 22 for an angled head of a dentist's boring machine. Further, the cylindrical surface of the head is knurled to facilitate manual turning thereof. Similarly, the cylindrical outer surface of the sleeve is knurled.

Although the tool is shown designed for screwing a pillar into place, it is obvious that the tool may be designed, through dimensional adjustment, for screwing another prosthetic part, such as a root screw 9 into place.

In use, the end 4 of the turning bolt is screwed into the prosthetic part to a position where the threads 5 are securely engaged in the hole of the pillar while the end does not reach the bottom thereof. The sleeve is brought into contact, by left-hand turning (anti-clockwise), via its end surface 18 against the pillar. The tool is gripped by the head thereof and the prosthetic part is screwed in a few revolutions into the root screw. If desired the turning may be continued via the connector 21 and a boring machine. Thereupon, the tool is released by left-handed turning, whereby the sleeve may be held by a wrench engaged over the cut recesses 15.

The tool according to the invention may also be used for releasing a prosthetic part, whereby the tool will be gripped and turned via the sleeve 13.

The tool may be manufactured by lathing of a metal such as stainless steel or titanium.

I claim:

1. A tool for screwing into place a threaded prosthetic part (6), which tool comprises a turning bolt (1) which has an elongated cylindrical core (2) having at one end thereof a head (3) for turning the tool, and having at its opposite end a portion (4) with first threads (5) for fitting into threads in the prosthetic part, and having second threads (11) on a portion (10) thereof between the ends thereof, whereby a sleeve (13) is arranged around the core, said sleeve having threads engaging said second threads, whereby the sleeve may be screwed into contact with the prosthetic part (6) and to locking of the tool in the prosthetic part, characterized in the pitch direction of said second threads is opposite to the pitch direction of the first threads.

2. A tool according to claim 1, characterized in that the second threads are arranged on a portion (10) of the core having a greater diameter than the threaded end portion (4) of the core, and that the sleeve (13) arranged around the core has a main portion in which the threads (12) are arranged, and an end portion (17) having a reduced diameter adjacent to the threaded end portion of the core.

* * * * *